United States Patent [19]

Calderoni et al.

[11] Patent Number: 5,091,556
[45] Date of Patent: Feb. 25, 1992

[54] PROCESS FOR PRODUCING CARBAMATES

[75] Inventors: Carlo Calderoni, Forlì; Franco Mizia; Franco Rivetti, both of Milan; Ugo Romano, Vimercate, all of Italy

[73] Assignee: Enichem Synthesis, S.p.A., Palermo, Italy

[21] Appl. No.: 500,405

[22] Filed: Mar. 28, 1990

[30] Foreign Application Priority Data

Apr. 7, 1989 [IT] Italy .............................. 20042 A/89

[51] Int. Cl.$^5$ .................... C07C 269/00; C07C 271/00
[52] U.S. Cl. ........................................ 560/24; 560/29; 560/115; 560/157; 560/160; 560/162
[58] Field of Search ................... 560/24, 29, 115, 157, 560/160, 162

[56] References Cited

U.S. PATENT DOCUMENTS

| | | | |
|---|---|---|---|
| 3,627,813 | 3/1972 | Abbote | 260/471 C |
| 3,763,217 | 10/1973 | Brill | 560/24 |
| 4,268,684 | 5/1981 | Gurgiolo | 560/24 |
| 4,381,404 | 4/1983 | Buvsch et al. | 560/24 |
| 4,550,188 | 10/1985 | Frulla et al. | 560/24 |
| 4,567,287 | 1/1986 | Frulla et al. | 560/24 |

FOREIGN PATENT DOCUMENTS

A298636 6/1988 European Pat. Off. .

Primary Examiner—Jose G. Dees
Assistant Examiner—Porfirio Nazario
Attorney, Agent, or Firm—Shea & Gold

[57] ABSTRACT

A process for preparing carbamates is disclosed, in which:
- a stoichiometric or higher-than-stoichiometric amount of an alkyl carbonate or a cycloalkyl carbonate is reacted with an aliphatic, cycloaliphatic or aromatic amine, in a first reaction step, by operating in the presence of a carbamation catalyst, in order to produce a mixture of a carbamate and an urea,
- the urea contained in the reaction product from the first process step is reacted with carbonate, in a second reaction step, in order to produce the corresponding carbamate, and
- the reaction mixture coming from the second process step is submitted to treatments in order to recover the carbamate.

The process makes it possible high yields and high values of selectivity to the useful reaction product to be obtained.

20 Claims, 1 Drawing Sheet

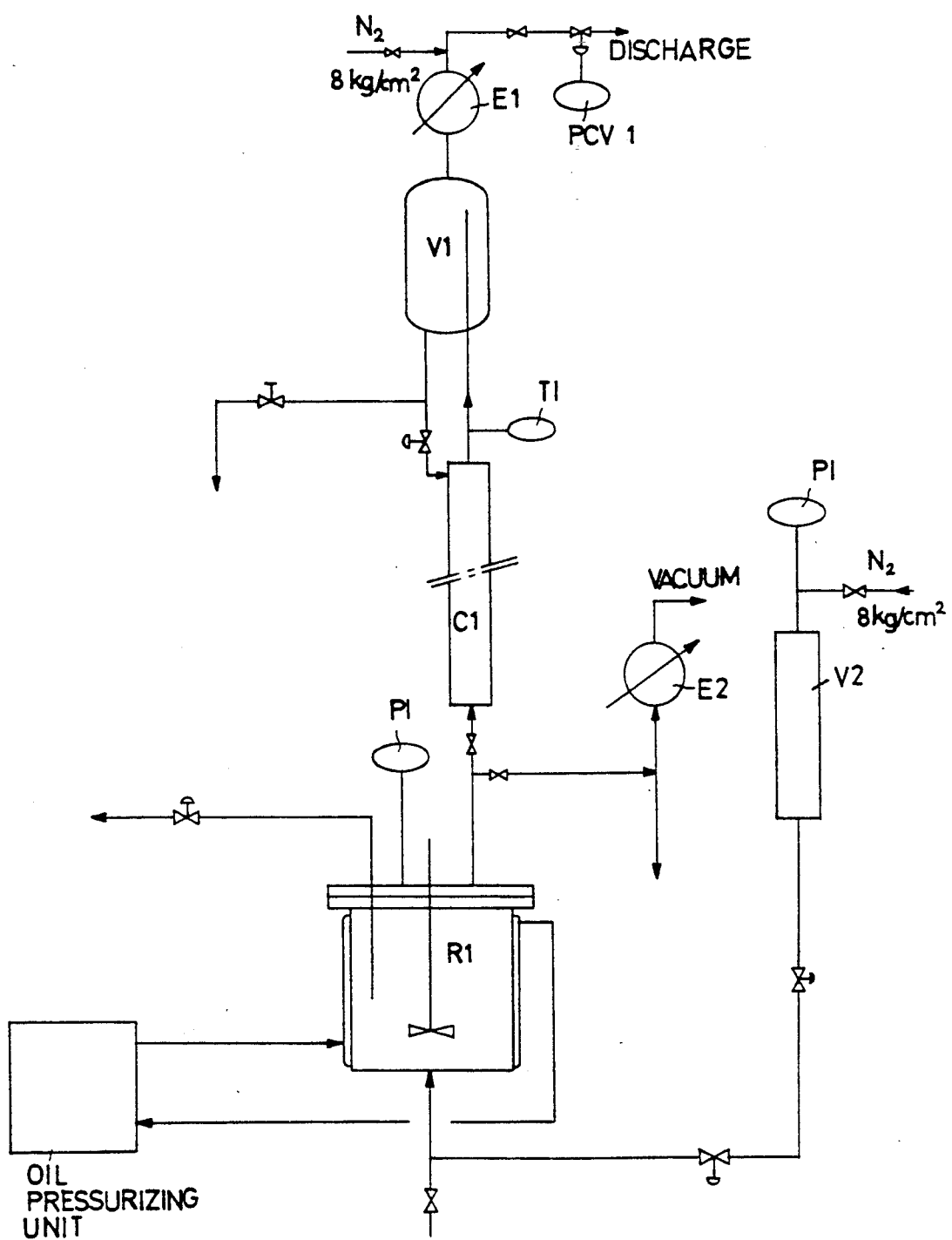

PROCESS FOR PRODUCING CARBAMATES

The present invention relates to a process for producing a carbamate by starting from a carbonate and an amine, which process makes it possible high yields and high values of selectivity to the useful reaction product to be obtained.

Carbamates are well-known products used in the art in particular in the sector of the plant protection products.

Various processes are known, which make it possible carbamates to be obtained by means of the reaction of a carbonate and an aromatic amine in the presence of a catalyst consisting of a Lewis' acid. So, e.g., U.S. Pat. No. 4,268,683 discloses the preparation of mono- and di-carbamates by means of the reaction, at about 150° C., of an alkyl carbonate and an aromatic mono- or di-amine, using as the Lewis' acid a compound of divalent Sn or divalent Zn, such as, e.g., Sn-(II) or Zn-(II) halides or salts of monovalent organic acids with a pKa equal to, or higher than 2.8. By operating in the presence of 5 mol % of catalyst, as referred to the amine, the yield of carbamate is of the order of 98%.

U.S. Pat. No. 4,268,684 discloses the preparation of carbamates by means of the reaction, at temperatures of the order of 200° C., of an alkyl carbonate with an aromatic mono- or di-amine, using as the Lewis' acid a compound of divalent Sn, divalent Zn, or divalent Co, with organic bicarboxy acids and/or having a pKa value equal to, or lower than, 2.8. By operating with 5 mol % of catalyst relatively to the amine, the yield to carbamate is of the order of 87%.

U.S. Pat. No. 4,550,188 discloses the preparation of mono- and di-carbamates by means of the reaction, at temperatures of the order of 200° C., of an alkyl carbonate with an aromatic mono- or di-amine, in the presence of a catalyst of aluminum metal, with promoters constituted by mercury and iodine salts. Under such conditions, if one operates with 20 mol % of aluminum, the yields to carbamate are of the order of 93%.

Japanese patent 55 00 4316 discloses the preparation of carbamates by means of the reaction of an alkyl carbonate and a primary or secondary aromatic mono-amine in the presence of a catalyst consisting of a compound of tetravalent Sn bonded to two butyl radicals and to two radicals, which can be either equal to, or different from, each other, selected from halogens, radicals of monovalent organic acids, alkoxides and oxygen.

U.S. Pat. No. 3,763,217 discloses the preparation of carbamates by means of the reaction, under refluxing conditions, of an alkyl carbonate with an aromatic amine, by using as a Lewis' acid 1 mol % of uranyl nitrate, as computed relatively to the amine. Under these conditions, the yields to carbamate are of the order of 20%. In none of the above cited patents mention is made of the possibility of producing carbamates by starting from aliphatic and cycloaliphatic amines, by operating in the presence of a Lewis' acid. Furthermore, when said Lewis' acid is used in a low molar ratio relatively to the amine, considerable amounts are unavoidingly formed of urea byproduct, also in case high molar ratios of the carbonate to the aromatic amine are used. Therefore, the obtainment of high yields of carbamates implies the need of operating with large catalyst contents, that constitutes a disadvantage from the economic viewpoint and from the viewpoint of the treatments of separation and purification of the end products.

From the prior art, processes are furthermore known for the production of carbamates by means of the reaction of an alkyl carbonate with a symmetrical urea by operating in the presence of a catalyst. So, e.g., U.S. Pat. No. 3,627,813 discloses the preparation of carbamates by means of the reaction of an alkyl carbonate with a symmetrical, alkyl or aryl urea by operating in chloroform under refluxing conditions. The reaction is catalysed by tertiary nitrogen and yields of the order of 80% are obtained. U.S. Pat. No. 4,381,404 discloses the preparation of carbamates by means of the reaction between an alkyl carbonate and a mono- or poly-substituted urea or polyurea with alkyl and/or aryl radicals. The reaction takes place at a temperature of the order of 180° C., in the presence of catalysts constituted by Lewis' acids and proceeds with a nearly quantitative yield. U.S. Pat. No. 4,567,287 discloses the preparation of carbamates by means of the reaction of an alkyl carbonate with an aromatic symmetrical or asymmetrical urea or polyurea. The reaction takes place at temperatures of the order of 130° C., in the presence of a catalyst of aluminum metal, with promoters constituted by mercury or iodine compounds. In none of these patents the transformation of urea is carried out by starting from a reaction mixture per se rich of carbamate.

The instant Applicant has found now a simple and advantageous process which makes it possible carbamates to be prepared from carbonates and aliphatic, cycloaliphatic or aromatic amines, with practically quantitative yields and selectivities into the useful reaction product, independently, to a large extent, from the molar ratio of the carbonate to the amine and operating with small amounts of carbamation catalyst.

In accordance therewith, the present invention relates to a process for preparing a carbamate (I):

wherein
R is a $(C_1-C_{18})$-alkyl radical with a linear or a branched chain, optionally containing one or more ethylenic unsaturation(s); a $(C_5-C_7)$-cycloalkyl radical; a monocyclic or polycyclic aryl radical, with the polycyclic aryl radicals being of either condensed-ring or non-condensed-ring types; or a $(C_1-C_4)$-alkylaryl radical; with said radicals optionally bearing one or more substituents not interfering with the reaction of carbamation, and
R' is a $(C_1-C_{12})$-alkyl radical with a linear or a branched chain, or a $(C_5-C_7)$-cycloalkyl radical,
by means of the reaction of a carbonate (II):

with an amine (III):

wherein R and R' have the same meaning as specified hereinabove,
by operating in the presence of a catalyst, characterized in that:

in a first reaction step the carbonate (II) and the amine (III) are reacted with each other in a mutual molar ratio comprised within the range of from 1/1 to 15/1, in the presence of a catalyst constituted by a Lewis' acid, at a temperature comprised within the range of from 90° to 140° C., under boiling conditions, with the alcohol $$R'\!-\!OH \qquad (V)$$

obtained as a reaction byproduct being removed from the reaction medium, until the conversion of the amine (III) is complete or substantially complete, in order to form a mixture of carbamate (I) and of urea (IV) according to the reaction equations:

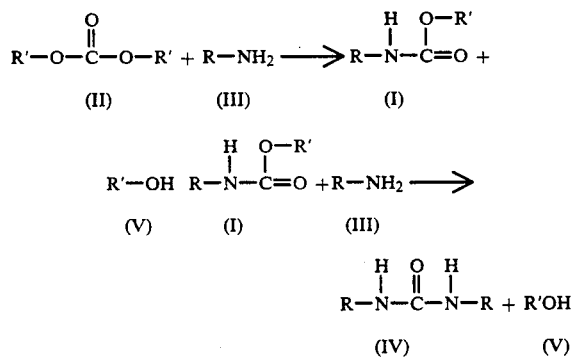

in a second reaction step, the urea contained in the mixture coming from said first step, either free or substantially free from amine (III) and alcohol (V), is reacted with carbonate (II), with a molar ratio of the carbonate (II) to the urea (IV) comprised within the range of from 20/1 to 80/1, at a temperature higher than 140° C., under the autogenous system pressure, with no removal of mixture constituents, in order to convert the urea (IV) into the carbamate (I) according to the equation:

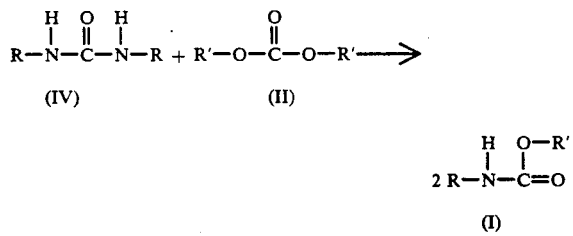

in a third reaction step the carbamate (I) is recovered from the mixture coming from the second reaction step.

Examples of ($C_1$-$C_{18}$)-alkyl radicals for R are: methyl, ethyl, propyl, hexyl, heptyl, octadecyl, propenyl, butenyl and octadecenyl. The ($C_5$-$C_7$)-cycloalkyl radicals for R are: cyclopentyl, cyclohexyl and cycloheptyl. Examples of aryl radical for R are phenyl and naphthyl. An example of ($C_1$-$C_4$)-alkylaryl radical for R is: benzyl. The above listed radicals R can possibly bear one or more substituents not interfering with the reaction of carbamation, selected from among ($C_1$-$C_4$)-alkyl radicals, ($C_1$-$C_4$)-alkoxy radicals, carbo-($C_1$-$C_4$)-alkoxy radicals, nitro groups and halogens, particularly fluorine, chlorine and bromine.

Examples of ($C_1$-$C_{12}$)-alkyl radicals for R' are: methyl, ethyl, propyl, isopropyl, butyl, hexyl and dodecyl. The ($C_5$-$C_7$)-cycloalkyl radicals for R' are: cyclopentyl, cyclohexyl and cycloheptyl.

Examples of carbonates (II) which can be used in the process according to the present invention are: dimethyl carbonate, diethyl carbonate, dipropyl carbonate, dibutyl carbonate, diisopropyl carbonate and dihexyl carbonate. Examples of amines (III) which can be used in the process according to the present invention are aniline, 3,4-dichloroaniline, alpha,alpha',alpha''-trifluorometatoluidine, ortho-, meta- and para-toluidine, 2,4-xylidine, 3,4-xylidine, 2,5-xylidine, 3-propyl-aniline, 4-isopropyl-aniline, methyl-amine, ethyl-amine, propyl-amine, isopropyl-amine, butyl-amine, heptyl-amine, cyclohexyl-amine, cyclopentyl-amine and cycloheptylamine.

Examples of carbamates (I) which can be prepared by means of the process according to the present invention are: methyl N-phenyl-carbamate, butyl N-phenyl-carbamate, pentyl N-phenyl-carbamate, hexyl N-phenyl-carbamate, methyl N-p-methoxyphenyl-carbamate, methyl N-p-bromophenyl-carbamate, isopropyl N-phenyl-carbamate, isopropyl N-p-chlorophenyl-carbamate, isopropyl N-m-trifluoromethyl-phenyl-carbamate, methyl N-isopropyl-carbamate, methyl N-sec.-butyl-carbamate and methyl N-cyclohexyl-carbamate.

According to the process of the instant invention, in a first reaction step a carbonate (II) and an amine (III) are reacted with each other in the presence of a catalyst in order to produce a mixture of carbamate (I) and urea (IV). More in particular, in said reaction a molar ratio of carbonate (II) to the amine (III) in the fed reactants is used, which is generally comprised within the range of from 1/1 to 15/1, and preferably will be kept comprised within the range of from 2/1 to 10/1. The reaction temperatures can advantageously be comprised within the range of from 90° to 140° C. Temperatures lower than the above specified first temperature limit value can be used, but are disadvantageous owing to the too low reaction speed, whilst temperatures higher than above specified second temperature limit value are disadvantageous in that they favour the formation of aminic groups bearing substituents on their nitrogen atom, besides the urea (IV). Preferably, temperatures of the order of 100° C. will be used in case of aliphatic or cycloaliphatic amines (III), and temperatures of the order of 130° C. will be used in case or amines (III) of aromatic nature.

The carbamation catalysts suitable of the intended purpose are generally constituted by Lewis' acids, such as divalent tin and divalent zinc chlorides, or salts of said metals with mono- or bi-carboxy organic acids, or compounds of trivalent iron, such as ferric chloride and ferric acetylacetonate. Among the compounds of divalent tin and zinc, Sn-(II) chloride will be preferably used in case amines (III) of aliphatic or cycloaliphatic nature are used, and zinc acetate will be preferably used in case of aromatic amines (III). The amount of catalyst used can be comprised within the range of from 0.01 to 0.15 mol, and preferably of from 0.01 to 0.07 mol, per each mol of amine (III).

In the first step of the process according to the present invention, the reaction is carried out under boiling conditions, with the alcohol (V) obtained as a reaction by-product being continuously removed, optionally as an azeotropic mixture with carbonate (II). The pressure under which the reaction is carried out depends on the vapour pressure of the alcohol (V) or, possibly, of its azeotropic mixture with the carbonate (II), at the temperature at which the reaction is carried out, and will anyway be such as to make it possible them to be removed by boiling from the reaction medium. In some cases, in order to decrease the reaction time, the addition of alcohol (V) to the reactants charged to the reaction was found to be advantageous. The amount of such an addition will be anyway small, and such that an amount of from 0.1 to 0.5 mol of alcohol (V) per each mol of amine (III), and preferably an amount of the order of 0.1 mol of alcohol (V) per each mol of amine (III) will be contained in the reaction medium. By operating under such above conditions, a complete conversion of the amine (III) is generally obtained within reaction times of the order of from 1 to 15 hours.

The reaction of the first step of the process can be carried out inside a stainless-steel autoclave equipped with a column for alcohol (V) removal. The operating pressure can be regulated by means of a pressure regulator installed downstream the condenser of the column and will anyway be secured by feeding to the reactor a nitrogen stream under the suitable pressure. In practice, the carbonate (II) and the amine (III) can be pre-mixed and to the so-obtained mixture the catalyst, and possibly the alcohol (V) can be added. The whole reaction mixture is charged to the autoclave, which is then heated up to the operating temperature. During the course of the reaction it is recommended to replenish the content of carbonate (II), with a make-up volume thereof being added, which is equivalent to the volume of condensate collected during the process, so as to keep constant the volume of the reaction mixture which, in particular in case in the azeotropic mixture alcohol (V)/carbonate (II) is distilled off, would tend to considerably decrease, with negative consequences on the selectivity of the reaction.

In any case, the reaction of the first step of the process leads to the formation of a mixture of a carbamate (I) and an urea (IV), with the amount of this latter possibly ranging from 5 to 15 mol % relatively to the mol of reacted amine (III), as a function of the selected reaction conditions.

In the second step of the process according to the present invention, the reaction mixture coming from the first step, free, or substantially free from the alcohol (V) and the amine (III), is treated in order to transform urea (IV) into carbamate (I). Typically, this mixture contains from 10 to 20 mol of carbamate and from 25 to 80 mol of unaltered carbonate (II) per each mol of urea (IV), besides the carbamation catalyst and traces of the amine (III). The second-step reaction is hence carried out with a molar ratio of carbonate (II) to the urea (IV) comprised within the range of from 20/1 to 80/1. If so needed, a replenishment of carbonate (II) can be carried out. The reaction temperature will be kept at values higher than 140° C., and of up to 180° C., by operating under the system's autogenous pressure and without removing any consituents from the reaction mixture. Temperatures lower than the above specified first temperature limit value are disadvantageous owing to too low values of the reaction speed, and temperatures higher than above specified second temperature limit value are undesired, in that they favour the taking place of a secondary reaction leading to a carbamate disubstituted to the nitrogen atom. The preferred value for the reaction temperature is of the order of 160° C. Under these conditions, the required times for a complete, or substantially complete, conversion of the urea (IV) into carbamate (I) are in general of the order of from 2 to 10 hours.

In practice, the second step of the process can be carried out inside the autoclave used for the first process step, adjusted at the suitable conditions of temperature and pressure.

In the third step of the process according to the present invention, the carbamate (I) contained in the mixture coming from the second step is isolated and purified. The operations are advantageously carried out in two steps, i.e., the residual carbonate (II) is first removed, and the carbamate (I) is then purified.

The removal of carbonate (II) is suitably carried out by evaporating the reaction mixture. In practice, at the end of the second process step the pressure inside the system is slowly lowered, with the temperature of the bottom being decreased down to 90°–130° C. and preferably down to about 110° C., and the system is kept under these conditions, with the carbonate (II) being distilled off until its removal is practically complete. The carbamate (I) is then distilled by operating under a still more reduced pressure.

The process according to the present invention makes it basically possible the advantage to be achieved, that the amine (III) is transformed into the relevant carbamate (I) with practically quantitative yields, independently, to a large extent, from the molar ratio of the carbonate (II) to the amine (III), with reduced amounts of Lewis' acid catalyst being consumed. This results into evident advantages as relates to the economy of the process, including the treatment of the waste liquors containing the exhausted catalyst and the improvement of the specific consumptions of the catalyst and of the amine (III).

In the following experimental examples, which are reported in order to better illustrate the invention, the apparatus was used, which is schematically depicted in the figure of the hereto attached drawing table. In this figure, with R1 an autoclave equipped with stirring means and heat exchange means is indicated; E1 and E2 respectively indicate a tap-water-cooled condenser and a brine-cooled condenser; with PVC1 a pressure regulator, with C1 a distillation column, with V1 a reflux accumulator and with V2 a carbonate make-up tank are indicated.

EXAMPLE 1 (COMPARATIVE EXAMPLE)

Referring to the figure of the hereto attached drawing table, 72 g (0.77 mol) of aniline, 226 g (2.5 mol) of dimethyl carbonate, 2.5 g (0.078 mol) of methanol and 1.2 g (0.006 mol) of anhydrous zinc acetate are charged to the reactor R1 (E2 intercepted; C1-E1 connected). The pressure inside the reaction equipment is then adjusted at 2 abs.atm and the temperature is then increased up to 130° C. The reaction is continued for 6 hours, with a mixture constituted by the azeotropic mixture of methanol and methyl acetate and by the azeotropic mixture of methanol and dimethyl carbonate being continuously distilled off. As the conversion proceeds, the pressure is gradually decreased from 2 to 0.5 abs.atm, so as to constantly keep the reaction mixture under boiling conditions.

At the end of the reaction time, two condensate fractions are collected: 32 g of a fraction formed by methanol (64.5% by weight), dimethyl carbonate (34.5% by weight) and methyl acetate (0.63% by weight); and 50.3 g of a fraction containing methanol (10.3% by weight) and dimethyl carbonate (89.7% by weight). The reaction mixture (198 g) contains 51.8% by weight of methyl N-phenyl-carbamate, 4.13% by weight of diphenylurea, 42.5% by weight of dimethyl carbonate and 0.05% by weight of aniline.

From these results, the following values of conversion and selectivity can be computed:

| aniline conversion: | 99.86% |
|---|---|
| selectivity to methyl N-phenyl-carbamate: | 88.1% by mol |
| selectivity to diphenyl-urea: | 10.0% by mol |

EXAMPLE 2

The process is carried out under the same conditions of Example 1, with 93.14 g (1.0 mol) of aniline, 270 g (3.0 mol) of dimethyl carbonate, 3.2 g (0.1 mol) of methanol and 1.8 g (0.01 mol) of zinc acetate being reacted with one another, in a first reaction step, at 130° C., for 6 hours.

At the end of the first reaction step, 160 g (1.78 mol) of dimethyl carbonate is added to the reaction mixture, while this latter is kept stirred at 130° C. The reactor R1 is intercepted, and the temperature is increased up to 165° C.; the reaction mixture is allowed to react, in a second reaction step, for 6 hours, under its autogenous pressure of 6 abs.atm.

At the end of the second reaction step, the pressure inside the reactor R1 is slowly decreased (E2 at 5° C.; C1 intercepted), until a residual pressure of 30 mmHg is reached, at the temperature of 110° C. Under these conditions, the unreacted dimethyl carbonate is removed from the reaction mixture. Then the temperature in E2 is increased up to 50° C., and the pressure is decreased down to 7 mmHg at 110° C. The distillation of methyl N-phenyl-carbamate is completed by progressively heating the reactor R1 up to 130° C. At the end of the operations, 150.2 g of 99.6%-pure methyl N-phenyl carbamate is obtained, which corresponds to 0.99 mol of 100%-pure product, with a yield of 99% by mol relatively to the initially charged aniline.

EXAMPLE 3

The process is carried out under the same conditions as of Example 1, with 135.1 g (1.0 mol) of para-isopropyl-aniline, 270 g (3 mol) of dimethyl carbonate, 3.2 g (0.1 mol) of methanol and 1.8 g (0.001 mol) of zinc acetate being reacted in a first reaction step at 130° C. for 6 hours.

At the end of the first reaction step 160 g (1.78 mol) of dimethyl carbonate is added and the reaction is continued in the same way as of Example 2 in the second and third reaction steps.

Under these conditions, 191 g of 99.7%-pure methyl N-p-cumyl carbamate is obtained, which corresponds to 0.985 mol of 100%-pure product, with a yield of 98.5% by mol relatively to the initially charged para-isopropyl-aniline.

EXAMPLE 4 (COMPARATIVE EXAMPLE)

99 g (1.0 mol) of cyclohexyl-amine, 863 g (9.6 mol) of dimethyl carbonate and 14.3 g (0.075 mol) of anhydrous stannous chloride are charged to reactor R1 (E2 intercepted; C1-E1 connected).

The system, under atmospheric pressure, is heated up to the boiling temperature (about 96° C.). The reaction is continued for 6 hours, with the azeotropic mixture of methanol/dimethyl carbonate being continuously distilled, with dimethyl carbonate being simultaneously replenished in R1 in a volume equivalent to the volume of collected condensate.

At the end of the reaction time about 41 g of condensate is collected, which contains 64% by weight of methanol. The resulting reaction mixture (933 g) contains 14.3% by weight of methyl N-cyclohexyl-carbamate, 2.4% by weight of N,N'-dicyclohexyl-urea, 81% by weight of dimethyl carbonate and 2.3% by weight of catalyst.

From the preceding data, the following values of conversion and selectivity can be computed:

| conversion of cyclohexyl-amine: | 100% |
|---|---|
| selectivity to methyl N-cyclo-hexyl-carbamate: | 85% by mol |
| selectivity to N,N'-dicyclohexyl-urea: | 10% by mol |

EXAMPLE 5

The process is carried out in the same way as of Example 4, with 99 g (1.0 mol) of cyclohexyl-amine, 863 g (9.6 mol) of dimethyl carbonate and 14.3 g (0.075 mol) of stannous chloride being reacted for 6 hours in a first reaction step under atmospheric pressure and at boiling temperature.

After the end of the first reaction step, the reactor R1 is intercepted and is heated up to 160° C., with the process being carried out in the second step for 4 hours, in the same way as of Example 2.

At the end of the second reaction step, methyl N-cyclohexyl-carbamate is isolated and purified by operating in the same way as of Example 2, with E2 being kept at 75° C.

Under these conditions, 144 g of carbamate is obtained, which corresponds to 0.917 mol of 100%-pure product, with a yield of 91.7% by mol relatively to the cyclohexyl-amine initially charged to the reaction.

We claim:

1. A process for producing a carbamate (I), comprising:

(a) contacting a carbonate (II), an amine (III), and a Lewis acid catalyst, in a molar ratio of carbonate (II) to amine (III) of from about 1/1 to about 15/1, under boiling conditions at a temperature of from about 90° to about 140° C., and removing at least some of a byproduct alcohol (V) until said amine (III) is substantially converted, thereby reacting said carbonate (II) and amine (III) to produce a mixture of carbamate (I) and urea (IV) according to the following equations:

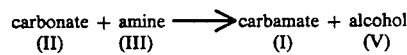

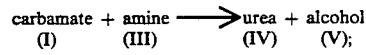

(b) contacting carbonate (II) and the urea (IV) of step (a) in a molar ratio of carbonate (II) to urea (IV) of from about 20/1 to about 80/1, under autogenous system pressure at a temperature of from 140° to 180° C., thereby converting the urea (IV) to carbamate (I) according to the following equation:

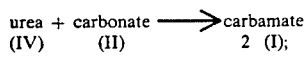

(c) recovering the carbamate (I) of step (b);
said carbamate (I) being represented by the formula

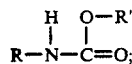

said carbonate (II) being represented by the formula

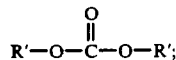

said amine (III) being represented by the formula

said urea (IV) being represented by the formula

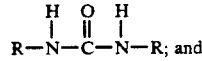

said alcohol (V) being represented by the formula

wherein R is selected from the group consisting of a ($C_1$-$C_{18}$)-alkyl radical with a linear chain, a ($C_1$-$C_{18}$)-alkyl radical with a branched chain, a ($C_5$-$C_7$)-cycloalkyl radical, a monocyclic aryl radical, a condensed-ring polycyclic aryl radical, a non-condensed-ring polycyclic aryl radical, and a ($C_1$-$C_4$)-alkylaryl radical; and wherein R' is selected from the group consisting of a linear chain ($C_1$-$C_{12}$)-alkyl radical, a branched chain ($C_1$-$C_{12}$)-alkyl radical, and a ($C_5$-$C_7$)-cycloalkyl radical.

2. A process as defined in claim 1, wherein said urea (IV) of step (b) is substantially free from amine (III) and alcohol (V), and wherein there is no removal of carbonate (II), urea (IV), or carbamate (I) in step (b).

3. A process as defined in claim 1, wherein said R is selected from the group consisting of a ($C_1$-$C_{18}$)-alkyl radical with a linear chain and a ($C_1$-$C_{18}$)-alkyl radical with a branched chain, and wherein said R further comprises at least one ethylenic unsaturation.

4. A process as defined in claim 1, wherein said R further comprises at least one unit selected from the group consisting of ($C_1$-$C_4$)-alkyl radicals, ($C_1$-$C_4$)-alkoxy radicals, carbon-($C_1$-$C_4$)-alkoxy radicals, nitro groups, and halogens.

5. A process as defined in claim 4, wherein R further comprises at least one halogen selected from the group consisting of fluorine, chlorine and bromine.

6. A process as defined in claim 1, wherein said R is a radical selected from the group consisting of methyl, ethyl, propyl, hexyl, heptyl, octadecyl, propenyl, butenyl, octadecenyl, cyclopentyl, cyclohexyl, cycloheptyl, phenyl, naphthyl, and benzyl.

7. A process as defined in claim 6, wherein said R further comprises at least one unit selected from the group consisting of ($C_1$-$C_4$)-alkyl radicals, ($C_1$-$C_4$)-alkoxy radicals, carbon-($C_1$-$C_4$)-alkoxy radicals, nitro groups, fluorine, chlorine and bromine.

8. A process as defined in claim 1, wherein said R' is a radical selected from the group consisting of methyl, ethyl, propyl, isopropyl, butyl, hexyl, dodecyl, hexadecyl, cyclopentyl, cyclohexyl and cycloheptyl.

9. A process as defined in claim 1, wherein said carbamate (I) is selected from the group consisting of methyl N-phenyl-carbamate, butyl N-phenyl-carbamate, pentyl N-phenyl-carbamate, hexyl N-phenyl-carbamate, methyl N-p-methoxyphenyl-carbamate, methyl N-p-bromophenyl-carbamate, isopropyl N-phenyl-carbamate, isopropyl N-p-chlorophenyl-carbamate, isopropyl N-m-trifluoromethyl-phenyl-carbamate, methyl N-isopropyl-carbamate, methyl N-sec.-butyl-carbamate, and methyl N-cyclohexyl-carbamate.

10. A process as defined in claim 1, wherein said carbonate (II) is selected from the group consisting of dimethyl carbonate, diethyl carbonate, dipropyl carbonate, dibutyl carbonate, diisopropyl carbonate, and dihexyl carbonate.

11. A process as defined in claim 1, wherein said amine (III) is selected from the group consisting of aniline, 3,4-dichloroaniline, alpha, alpha', alpha"-trifluoro-matatoluidine, ortho-toluidine, meta-toluidine, para-toluidene, 2,4-xylidine 3,4-xylidine, 2,5-xylidine, 3-propyl-aniline, 4-isopropyl-aniline, methyl-amine, ethyl-amine, propyl-amine, isopropyl-amine, butyl-amine, heptyl-amine, cyclohexyl-amine, cyclopentyl-amine, and cycloheptyl-amine.

12. A process as defined in claim 1, wherein said molar ratio of step (a) is from about 2/1 to about 10.1

13. A process as defined in claim 1, wherein said catalyst is in an amount of from about 0.01 to about 0.15 moles for each mole of amine (III).

14. A process as defined in claim 13, wherein said catalyst is in an amount of from about 0.01 to about 0.07 moles for each mole of amine (III).

15. A process as defined in claim 1, wherein said Lewis acid catalyst is selected from the group consisting of divalent tin chlorides, divalent zinc chlorides, tin salts with mono-carboxy acids, zinc salts with mono-carboxy acids, tin salts with bi-carboxy acids, zinc salts with bi-carboxy acids, ferric chloride, and ferric acetylacetonate.

16. A process as defined in claim 1, wherein step (a) comprises further contacting said carbonate (II), amine (III), and Lewis acid catalyst with an alcohol (V), said alcohol being in an amount of from about 0.1 to about 0.5 moles for each mole of amine (III).

17. A process as defined in claim 16, wherein said alcohol is in an amount of about 0.1 moles for each mole of amine.

18. A process as defined in claim 1, wherein step (b) is conducted at a temperature of about 160° C.

19. A process as defined in claim 1, wherein said amine (III) is selected from the group consisting of aliphatic amines and cycloaliphatic amines; said catalyst is a divalent tin chloride; and said temperature of step (a) is about 100° C.

20. A process as defined in claim 1, wherein said amine (III) is an aromatic amine; said catalyst is zinc acetate; and said temperature of step (a) is about 130° C.

* * * * *